United States Patent [19]

Hampel et al.

[11] Patent Number: 5,683,902

[45] Date of Patent: Nov. 4, 1997

[54] HUMAN PAPILLOMA VIRUS INHIBITION BY A HAIRPIN RIBOZYME

[75] Inventors: Arnold Hampel, DeKalb, Ill.; Joseph DiPaolo, Bethesda, Md.; Andrew M. Siwkowski, Sycamore; Scott C. Galasinski, Rockford, both of Ill.

[73] Assignees: Northern Illinois University, DeKalb, Ill.; United States of America as represented by the Department of Health and Human Services, Washington, D.C.

[21] Appl. No.: 410,005

[22] Filed: Mar. 21, 1995

Related U.S. Application Data

[63] Continuation of Ser. No. 242,665, May 13, 1994, abandoned.

[51] Int. Cl.[6] .................. C12P 19/34; C12N 15/00; C12N 5/00; C07H 21/02
[52] U.S. Cl. ............... 435/240.2; 435/6; 435/91.31; 435/172.1; 435/172.3; 435/240.1; 435/320.1; 514/44; 536/23.2; 536/24.5; 536/25.3
[58] Field of Search .................. 435/91.31, 91.4, 435/172.1, 172.3, 320.1, 240.1, 240.2; 514/44; 536/23.1, 24.1, 24.5, 25.3; 935/77, 78

[56] References Cited

PUBLICATIONS

Altschuler et al., 1992, Gene 122:85–90, "A method for generating transcripts with defined 5'and 3'termini by autolytic processing".
Anderson et al., 1994, Nucleic Acids Research 22(6):1096–1100, "Mutagenesis of the haripin ribozyme".
Cepko et al., 1984, Cell, 37:1053–1062, "Construction and Applications of a Highly Transmissible Murine Retrovirus Shuttle Vector" (Jul.).
Chatterjee and Wong, 1993, Methods: Companion to Methods in Enzymology 5(1):51–59, "Adeno–Associated Viral Vectors for Delivery of Antisense RNA".
Cheong et al., 1990, Nature 346:680–682, "Solution structure of an unusually stable RNA hairpin, 5'GGAC(UUCG)GUCC".
Das et al., 1988, Embo Journal 7(2):503–512, "Upstream regulatory elements are necessary and sufficient for transcription of U6 RNA gene by RNA polymerase III".
Dipaolo et al., 1993, Critical Reviews in Oncogenesis 00:1–23, "Cellular and Molecular Alteratins in Human Epithelial Cells Transformed by Recombinant Human Papillomavirus DNA".
Doeberitz et al., 1992, Int. J. Cancer, 51:831–834, "Inhibition of tumorigenicity of cervical cancer cells in nude mice by HPV E6–E7 anti–sense RNA".
Felgner et al., 1993, Methods: Companion to Methods in Enzymology 5(1):67–75, "Cationic Lipid–Mediated Delivery of Polynucleotides".
Forster and Symons, 1987, Cell 49:211–220, "Self–Cleavage of Plus and Minus RNAs of a Virusoid and Structural Model for the Active Sites".
Hampel and Tritz, 1989, Biochem. 28:4929–4933, "RNA Catalytic Properties of the Minimum (–)sTRSV Sequence".

Hampel et al., 1990, Nucleic Acids Res. 18:299–304, "Hairpin catalytic RNA model: evidence for helices and sequence requirement for substrate RNA".
Haseloff and Gerlach, 1988, Nature 334:585–591, "Simple RNA enzymes with new and highly specific endoribonuclease activies" (Aug.).
Mulligan, 1993, Science, 260:926–932, "The Basic Science of Gene Therapy" (May).
Nasseri et al., 1991, Virology 184:131–140, "Human Papillomavirus Type 16 Immortalized Cervical Keratinocytes Contain Transcripts Encoding E6, E7, and E2 Initiated at the P97 Promoter . . .".
Ojwang et al., 1992, Proc. Natl. Acad. Sci 89:10802–10806, "Introductory Remarks on the General Application of Antisense".
Rossi, 1993, Methods: Companion to Methods in Enzymology 5:1–5, "Introductory Remarks on the General Application of Antisense RNAs and Ribozymes".
Sambrook, 1989, Molecular Cloning: A Laboratory Manual (Cold Spring Harbor Lab Press) 1.25–1.28; 1.60–1.61; 1.68–1.69; 1.82–1.84; 6.9–6.13, 6:46–6.48.
Sarver et al., 1990, Gene Regulation and Aids, pp. 305–325 "Exploring Catalytic RNAs (Ribozymes) as Anti–HIV Agents".
Sedman et al., 1991,J. Virology, 65:4860–4866, "The Full–Length E6 Protein of Human Papillomavirus Type 16 Has Transforming and trans–Activating Activies and Cooperates with E7 . . .".
Smotkin et al., 1989, J. Virology, 63:1441–1447, "Oncogenic and Nononcogenic Human Genital Papillomaviruses Generate the E7 mRNA by Different Mechanisms".
Smotkin and Wettstein, 1986, Proc. Nat. Acad. Sci. 83:4680–4684 "Transcription of human papillomavirus type 16 early genes in cervical cancer–derived cell line and identification of the E7 protein".
Steele et al., 1993, Cancer Research 53:2330–2337, "Effects of Human Papillomavirus Type 18–specific Antisense Oligonucleotides on the Transformed Phenotype of Human Carcinoma Cell Lines".
Storey et al., 1991, Nucleic Acids Research 19(15):4109–4114, "Anti–sense phosphorothioate oligonucleotides have both specific and non–specific effects on cells containing human papillomavirus type 16".
Sullivan, 1993, Methods: Companion to Methods in Enzymology 5(1):61–66"Liposome–Mediated Uptake of Ribozymes".
Uhlenbeck, 1987, Nature, 328:596–600, "A small catalytic oligoribonucleotide".
Varani et al., 1991, Biochem, 30:3280–3289, "Structure of an Unusually Stable RNA Hairpin".
Yu et al., 1993, Proc. Natl. Acad. Scie. 90:6340–6344, "A hairpin inhibits expression of diverse strains of human immunodeficiency virus type 1.".
He et al (1993) FEBS Letts. 322, 21–24.

Primary Examiner—George G. Elliott
Assistant Examiner—Sean McGarry
Attorney, Agent, or Firm—Kohn & Associates

[57] ABSTRACT

Synthetic catalytic RNAs, i.e. ribozyme, including a hairpin portion, binding sites for binding to a human papilloma virus after viral base 419 and 434, respectively, and cleavage sites for cleaving the virus at the binding sites have been constructed.

8 Claims, 7 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 7904 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Human papillomavirus
        ( B ) STRAIN: HPV16

( x i ) SEQUENCE DESCRIPTION: SEQ ID NO:1:

```
ACTACAATAA  TTCATGTATA  AAACTAAGGG  CGTAACCGAA  ATCGGTTGAA  CCGAAACCGG   60
TTAGTATAAA  AGCAGACATT  TTATGCACCA  AAAGAGAACT  GCAATGTTTC  AGGACCCACA  120
GGAGCGACCC  AGAAAGTTAC  CACAGTTATG  CACAGAGCTG  CAAACAACTA  TACATGATAT  180
AATATTAGAA  TGTGTGTACT  GCAAGCAACA  GTTACTGCGA  CGTGAGGTAT  ATGACTTTGC  240
TTTTCGGGAT  TTATGCATAG  TATATAGAGA  TGGGAATCCA  TATGCTGTAT  GTGATAAATG  300
TTTAAAGTTT  TATTCTAAAA  TTAGTGAGTA  TAGACATTAT  TGTTATAGTT  TGTATGGAAC  360
AACATTAGAA  CAGCAATACA  ACAAACCGTT  GTGTGATTTG  TTAATTAGGT  GTATTAACTG  420
TCAAAAGCCA  CTGTGTCCTG  AAGAAAAGCA  AAGACATCTG  GACAAAAAGC  AAAGATTCCA  480
TAATATAAGG  GGTCGGTGGA  CCGGTCGATG  TATGTCTTGT  TGCAGATCAT  CAAGAACACG  540
TAGAGAAACC  CAGCTGTAAT  CATGCATGGA  GATACACCTA  CATTGCATGA  ATATATGTTA  600
GATTTGCAAC  CAGAGACAAC  TGATCTCTAC  TGTTATGAGC  AATTAAATGA  CAGCTCAGAG  660
GAGGAGGATG  AAATAGATGG  TCCAGCTGGA  CAAGCAGAAC  CGGACAGAGC  CCATTACAAT  720
ATTGTAACCT  TTTGTTGCAA  GTGTGACTCT  ACGCTTCGGT  TGTGCGTACA  AAGCACACAC  780
GTAGACATTC  GTACTTTGGA  AGACCTGTTA  ATGGGCACAC  TAGGAATTGT  GTGCCCCATC  840
TGTTCTCAGA  AACCATAATC  TACCATGGCT  GATCCTGCAG  GTACCAATGG  GGAAGAGGGT  900
ACGGGATGTA  ATGGATGGTT  TTATGTAGAG  GCTGTAGTGG  AAAAAAAAAC  AGGGGATGCT  960
ATATCAGATG  ACGAGAACGA  AAATGACAGT  GATACAGGTG  AAGATTTGGT  AGATTTTATA 1020
GTAAATGATA  ATGATTATTT  AACACAGGCA  GAAACAGAGA  CAGCACATGC  GTTGTTTACT 1080
GCACAGGAAG  CAAAACAACA  TAGAGATGCA  GTACAGGTTC  TAAAACGAAA  GTATTTGGTA 1140
GTCCACTTAG  TGATATTAGT  GGATGTGTAG  ACAATAATAT  TAGTCCTAGA  TTAAAAGCTA 1200
TATGTATAGA  AAAACAAAGT  AGAGCTGCAA  AAAGGAGATT  ATTTGAAAGC  GAAGACAGCG 1260
GGTATGGCAA  TACTGAAGTG  GAAACTCAGC  AGATGTTACA  GGTAGAAGGG  CGCCATGAGA 1320
CTGAAACACC  ATGTAGTCAG  TATAGTGGTG  AAGTGGGGG   TGGTTGCAGT  CAGTACAGTA 1380
GTGGAAGTGG  GGGAGAGGGT  GTTAGTGAAA  GACACACTAT  ATGCCAAACA  CCACTTACAA 1440
ATATTTTAAA  TGTACTAAAA  ACTAGTAATG  CAAAGGCAGC  AATGTTAGCA  AAATTTAAAG 1500
AGTTATACGG  GGTGAGTTTT  TCAGAATTAG  TAAGACCATT  TAAAAGTAAT  AAATCAACGT 1560
GTTGCGATTG  GTGTATTGCT  GCATTTGGAC  TTACACCCAG  TATAGCTGAC  AGTATAAAAA 1620
CACTATTACA  ACAATATTGT  TTATATTTAC  ACATTCAAAG  TTTAGCATGT  TCATGGGGAA 1680
TGGTTGTGTT  ACTATTAGTA  AGATATAAAT  GTGGAAAAAA  TAGAGAAACA  ATTGAAAAAT 1740
TGCTGTCTAA  ACTATTATGT  GTGTCTCCAA  TGTGTATGAT  GATAGAGCCT  CCAAAATTGC 1800
GTAGTACAGC  AGCAGCATTA  TATTGGTATA  AAACAGGTAT  ATCAAATATT  AGTGAAGTGT 1860
ATGGAGACAC  GCCAGAATGG  ATACAAAGAC  AAACAGTATT  ACAACATAGT  TTAATGATT  1920
GTACATTTGA  ATTATCACAG  ATGGTACAAT  GGGCCTACGA  TAATGACATA  GTAGACGATA 1980
GTGAAATTGC  ATATAAATAT  GCACAATTGG  CAGACACTAA  TAGTAATGCA  AGTGCCTTTC 2040
```

```
TAAAAAGTAA  TTCACAGGCA  AAAATTGTAA  AGGATTGTGC  AACAATGTGT  AGACATTATA   2100
AACGAGCAGA  AAAAAAACAA  ATGAGTATGA  GTCAATGGAT  AAAATATAGA  TGTGATAGGG   2160
TAGATGATGG  AGGTGATTGG  AAGCAAATTG  TTATGTTTT   AAGGTATCAA  GGTGTAGAGT   2220
TTATGTCATT  TTTAACTGCA  TTAAAAGAT   TTTTGCAAGG  CATACCTAAA  AAAAATTGCA   2280
TATTACTATA  TGGTGCAGCT  AACACAGGTA  AATCATTATT  TGGTATGAGT  TTAATGAAAT   2340
TTCTGCAAGG  GTCTGTAATA  TGTTTGTAA   ATTCTAAAAG  CCATTTTGG   TTACAACCAT   2400
TAGCAGATGC  CAAAATAGGT  ATGTTAGATG  ATGCTACAGT  GCCCTGTTGG  AACTACATAG   2460
ATGACAATTT  AAGAAATGCA  TTGGATGGAA  ATTTAGTTTC  TATGGATGTA  AAGCATAGAC   2520
CATTGGTACA  ACTAAAATGC  CCTCCATTAT  TAATTACATC  TAACATTAAT  GCTGGTACAG   2580
ATTCTAGGTG  GCCTTATTTA  CATAATAGAT  TGGTGGTGTT  TACATTTCCT  AATGAGTTTC   2640
CATTTGACGA  AAACGGAAAT  CCAGTGTATG  AGCTTAATGA  TAAGAACTGG  AAATCCTTTT   2700
TCTCAAGGAC  GTGGTCCAGA  TTAAGTTTGC  ACGAGGACGA  GGACAAGGAA  AACGATGGAG   2760
ACTCTTTGCC  AACGTTTAAA  TGTGTGTCAG  GACAAAATAC  TAACACATTA  TGAAAATGAT   2820
AGTACAGACC  TACGTGACCA  TATAGACTAT  TGGAAACACA  TGCGCCTAGA  ATGTGCTATT   2880
TATTACAAGG  CCAGAGAAAT  GGGATTTAAA  CATATTAACC  ACCAAGTGGT  GCCAACACTG   2940
GCTGTATCAA  AGAATAAAGC  ATTACAAGCA  ATTGAACTGC  AACTAACGTT  AGAAACAATA   3000
TATAACTCAC  AATATAGTAA  TGAAAAGTGG  ACATTACAAG  ACGTTAGCCT  TGAAGTGTAT   3060
TTAACTGCAC  CAACAGGATG  TATAAAAAAA  CATGGATATA  CAGTGGAAGT  GCAGTTTGAT   3120
GGAGACATAT  GCAATACAAT  GCATTATACA  AACTGGACAC  ATATATATAT  TTGTGAAGAA   3180
GCATCAGTAA  CTGTGGTAGA  GGGTCAAGTT  GACTATTATG  GTTATATTA   TGTTCATGAA   3240
GGAATACGAA  CATATTTTGT  GCAGTTTAAA  GATGATGCAG  AAAAATATAG  TAAAAATAAA   3300
GTATGGGAAG  TTCATGCGGG  TGGTCAGGTA  ATATTATGTC  CTACATCTGT  GTTTAGCAGC   3360
AACGAAGTAT  CCTCTCCTGA  AATTATTAGG  CAGCACTTGG  CCAACCACCC  CGCCGCGACC   3420
CATACCAAAG  CCGTCGCCTT  GGGCACCGAA  GAAACACAGA  CGACTATCCA  GCGACCAAGA   3480
TCAGAGCCAG  ACACCGGAAA  CCCCTGCCAC  ACCACTAAGT  TGTTGCACAG  AGACTCAGTG   3540
GACAGTGCTC  CAATCCTCAC  TGCATTTAAC  AGCTCACACA  AAGGACGGAT  TAACTGTAAT   3600
AGTAACACTA  CACCCATAGT  ACATTTAAAA  GGTGATGCTA  ATACTTTAAA  ATGTTTAAGA   3660
TATAGATTTA  AAAAGCATTG  TACATTGTAT  ACTGCAGTGT  CGTCTACATG  GCATTGGACA   3720
GGACATAATG  TAAAACATAA  AAGTGCAATT  GTTACACTTA  CATATGATAG  TGAATGGCAA   3780
CGTGACCAAT  TTTTGTCTCA  AGTTAAAATA  CCAAAAACTA  TTACAGTGTC  TACTGGATTT   3840
ATGTCTATAT  GACAAATCTT  GATACTGCAT  CCACAACATT  ACTGGCGTGC  TTTTTGCTTT   3900
GCTTTGTGTG  CTTTTGTGTG  TCTGCCTATT  AATACGTCCG  CTGCTTTTGT  CTGTGTCTAC   3960
ATACACATCA  TTAATAATAT  TGGTATTACT  ATTGTGGATA  ACAGCAGCCT  CTGCGTTTAG   4020
GTGTTTATT   GTATATATTA  TATTTGTTTA  TATACCATTA  TTTTAATAC   ATACACATGC   4080
ACGCTTTTTA  ATTACATAAT  GTATATGTAC  ATAATGTAAT  TGTTACATAT  AATTGTTGTA   4140
TACCATAACT  TACTATTTTT  TCTTTTTTAT  TTTCATATAT  AATTTTTTTT  TTTGTTTGTT   4200
TGTTTGTTTT  TTAATAAACT  GTTATTACTT  AACAATGCGA  CACAAACGTT  CTGCAAAACG   4260
CACAAAACGT  GCATCGGCTA  CCCAACTTTA  TAAAACATGC  AAACAGGCAG  GTACATGTCC   4320
ACCTGACATT  ATACCTAAGG  TTGAAGGCAA  AACTATTGCT  GAACAAATAT  TACAATATGG   4380
AAGTATGGGT  GTATTTTTTG  GTGGGTTAGG  AATTGGAACA  GGGTCGGGTA  CAGGCGGACG   4440
```

```
CACTGGGTAT  ATTCCATTGG  GAACAAGGCC  TCCCACAGCT  ACAGATACAC  TTGCTCCTGT   4500
AAGACCCCCT  TTAACAGTAG  ATCCTGTGGG  CCCTTCTGAT  CCTTCTATAG  TTTCTTTAGT   4560
GGAAGAAACT  AGTTTTATTG  ATGCTGGTGC  ACCAACATCT  GTACCTTCCA  TTCCCCCAGA   4620
TGTATCAGGA  TTTAGTATTA  CTACTTCAAC  TGATACCACA  CCTGCTATAT  AGATATTAA    4680
TAATACTGTT  ACTACTGTTA  CTACACATAA  TAATCCCACT  TCACTGACC   CATCTGTATT   4740
GCAGCCTCCA  ACACCTGCAG  AAACTGGAGG  GCATTTTACA  CTTTCATCAT  CCACTATTAG   4800
TACACATAAT  TATGAAGAAA  TTCCTATGGA  TACATTTATT  GTTAGCACAA  ACCCTAACAC   4860
AGTAACTAGT  AGCACACCCA  TACCAGGGTC  TCGCCCAGTG  GCACGCCTAG  GATTATATAG   4920
TCGCACAACA  CAACAGGTTA  AAGTTGTAGA  CCCTGCTTTT  GTAACCACTC  CCACTAAACT   4980
TATTACATAT  GATAATCCTG  CATATGAAGG  TATAGATGTG  GATAATACAT  TATATTTTC    5040
TAGTAATGAT  AATAGTATTA  ATATAGCTCC  AGATCCTGAC  TTTTGGATA   TAGTTGCTTT   5100
ACATAGGCCA  GCATTAACCT  CTAGGCGTAC  TGGCATTAGG  TACAGTAGAA  TTGGTAATAA   5160
ACAAACACTA  CGTACTCGTA  GTGGAAAATC  TATAGGTGCT  AAGGTACATT  ATTATTATGA   5220
TTTAAGTACT  ATTGATCCTG  CAGAAGAAAT  AGAATTACAA  ACTATAACAC  CTTCTACATA   5280
TACTACCACT  TCACATGCAG  CCTCACCTAC  TTCTATTAAT  AATGGATTAT  ATGATATTTA   5340
TGCAGATGAC  TTTATTACAG  ATACTTCTAC  AACCCCGGTA  CCATCTGTAC  CCTCTACATC   5400
TTTATCAGGT  TATATTCCTG  CAAATACAAC  AATTCCTTTT  GGTGGTGCAT  ACAATATTCC   5460
TTTAGTATCA  GGTCCTGATA  TACCCATTAA  TATAACTGAC  CAAGCTCCTT  CATTAATTCC   5520
TATAGTTCCA  GGGTCTCCAC  AATATACAAT  TATTGCTGAT  GCAGGTGACT  TTTATTTACA   5580
TCCTAGTTAT  TACATGTTAC  GAAAACGACG  TAAACGTTTA  CCATATTTTT  TTTCAGATGT   5640
CTCTTTGGCT  GCCTAGTGAG  GCCACTGTCT  ACTTGCCTCC  TGTCCCAGTA  TCTAAGGTTG   5700
TAAGCACGGA  TGAATATGTT  GCACGCACAA  ACATATATTA  TCATGCAGGA  ACATCCAGAC   5760
TACTTGCAGT  TGGACATCCC  TATTTTCCTA  TTAAAAAACC  TAACAATAAC  AAAATATTAG   5820
TTCCTAAAGT  ATCAGGATTA  CAATACAGGG  TATTTAGAAT  ACATTTACCT  GACCCCAATA   5880
AGTTTGGTTT  TCCTGACACC  TCATTTTATA  ATCCAGATAC  ACAGCGGCTG  GTTTGGGCCT   5940
GTGTAGGTGT  TGAGGTAGGT  CGTGGTCAGC  CATTAGGTGT  GGGCATTAGT  GGCCATCCTT   6000
TATTAAATAA  ATTGGATGAC  ACAGAAAATG  CTAGTGCTTA  TGCAGCAAAT  GCAGGTGTGG   6060
ATAATAGAGA  ATGTATATCT  ATGGATTACA  AACAAACACA  ATTGTGTTTA  ATTGGTTGCA   6120
AACCACCTAT  AGGGGAACAC  TGGGGCAAAG  GATCCCCATG  TACCAATGTT  GCAGTAAATC   6180
CAGGTGATTG  TCCACCATTA  GAGTTAATAA  ACACAGTTAT  TCAGGATGGT  GATATGGTTC   6240
ATACTGGCTT  TGGTGCTATG  GACTTTACTA  CATTACAGGC  TAACAAAAGT  GAAGTTCCAC   6300
TGGATATTTG  TACATCTATT  TGCAAATATC  CAGATTATAT  TAAAATGGTG  TCAGAACCAT   6360
ATGGCGACAG  CTTATTTTTT  TATTTACGAA  GGGAACAAAT  GTTTGTTAGA  CATTTATTTA   6420
ATAGGGCTGG  TACTGTTGGT  GAAAATGTAC  CAGACGATTT  ATACATTAAA  GGCTCTGGGT   6480
CTACTGCAAA  TTTAGCCAGT  TCAAATTATT  TTCCTACACC  TAGTGGTTCT  ATGGTTACCT   6540
CTGATGCCCA  AATATTCAAT  AAACCTTATT  GGTTACAACG  AGCACAGGGC  CACAATAATG   6600
GCATTTGTTG  GGGTAACCAA  CTATTTGTTA  CTGTTGTTGA  TACTACACGC  AGTACAAATA   6660
TGTCATTATG  TGCTGCCATA  TCTACTTCAG  AAACTACATA  TAAAAATACT  AACTTTAAGG   6720
AGTACCTACG  ACATGGGGAG  GAATATGATT  TACAGTTTAT  TTTCAACTG   TGCAAAATAA   6780
CCTTAACTGC  AGACGTTATG  ACATACATAC  ATTCTATGAA  TTCCACTATT  TTGGAGGACT   6840
```

```
GGAATTTTGG  TCTACAACCT  CCCCCAGGAG  GCACACTAGA  AGATACTTAT  AGGTTTGTAA    6900
CCCAGGCAAT  TGCTTGTCAA  AAACATACAC  CTCCAGCACC  TAAAGAAGAT  GATCCCCTTA    6960
AAAAATACAC  TTTTTGGGAA  GTAAATTTAA  AGGAAAAGTT  TTCTGCAGAC  CTAGATCAGT    7020
TTCCTTTAGG  ACGCAAATTT  TTACTACAAG  CAGGATTGAA  GGCCAAACCA  AAATTTACAT    7080
TAGGAAAACG  AAAAGCTACA  CCCACCACCT  CATCTACCTC  TACAACTGCT  AAACGCAAAA    7140
AACGTAAGCT  GTAAGTATTG  TATGTATGTT  GAATTAGTGT  TGTTTGTTGT  GTATATGTTT    7200
GTATGTGCTT  GTATGTGCTT  GTAAATATTA  AGTTGTATGT  GTGTTTGTAT  GTATGGTATA    7260
ATAAACACGT  GTGTATGTGT  TTTTAAATGC  TTGTGTAACT  ATTGTGTCAT  GCAACATAAA    7320
TAAACTTATT  GTTTCAACAC  CTACTAATTG  TGTTGTGGTT  ATTCATTGTA  TATAAACTAT    7380
ATTTGCTACA  TCCTGTTTTT  GTTTTATATA  TACTATATTT  TGTAGCGCCA  GGCCCATTTT    7440
GTAGCTTCAA  CCGAATTCGG  TTGCATGCTT  TTTGGCACAA  AATGTGTTTT  TTTAAATAGT    7500
TCTATGTCAG  CAACTATGGT  TTAAACTTGT  ACGTTCCTG   CTTGCCATGC  GTGCCAAATC    7560
CCTGTTTTCC  TGACCTGCAC  TGCTTGCCAA  CCATTCCATT  GTTTTTACA   CTGCACTATG    7620
TGCAACTACT  GAATCACTAT  GTACATTGTG  TCATATAAAA  TAAATCACTA  TGCGCCAACG    7680
CCTTACATAC  CGCTGTTAGG  CACATATTTT  TGGCTTGTTT  TAACTAACCT  AATTGCATAT    7740
TTGGCATAAG  GTTTAAACTT  CTAAGGCCAA  CTAAATGTCA  CCCTAGTTCA  TACATGAACT    7800
GTGTAAAGGT  TAGTCATACA  TTGTTCATTT  GTAAAACTGC  ACATGGGTGT  GTGCAAACCG    7860
ATTTTGGGTT  ACACATTTAC  AAGCAACTTA  TATAATAATA  CTAA                      7904
```

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

ACUGUGUCCU GAAGA                                                          15

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

ACUGUGUCCU GAAGAA                                                         16

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

ACUGUGUCCU GAAGAAA                                                        17

( 2 ) INFORMATION FOR SEQ ID NO:5:

( i ) SEQUENCE CHARACTERISTICS:

(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:5:

GGACUUCGGU CC                                                                                12

(2) INFORMATION FOR SEQ ID NO:6:

(i) SEQUENCE CHARACTERISTICS:
(A) LENGTH: 60 base pairs
(B) TYPE: nucleic acid
(C) STRANDEDNESS: single
(D) TOPOLOGY: linear (xi) SEQUENCE DESCRIPTION: SEQ ID NO:6:

UUCUUCAGAG AACAGUACCA GAGAAACACA CGGACUUCGU CCGUGGUAUA UUACCUGGUA      60

(2) INFORMATION FOR SEQ ID NO:7:

(i) SEQUENCE CHARACTERISTICS:
(A) LENGTH: 14 base pairs
(B) TYPE: nucleic acid
(C) STRANDEDNESS: single
(D) TOPOLOGY: linear (xi) SEQUENCE DESCRIPTION: SEQ ID NO:7:

UAACUGUCAA AAGC                                                                              14

(2) INFORMATION FOR SEQ ID NO:8:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:8:

UAACUGUCAA AAGCC                                                                             15

(2) INFORMATION FOR SEQ ID NO:9:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:9:

UAACUGUCAA AAGCCA                                                                            16

(2) INFORMATION FOR SEQ ID NO:10:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:10:

UAACUGUCAA AAGCCAC                                                                           17

(2) INFORMATION FOR SEQ ID NO:11:

(i) SEQUENCE CHARACTERISTICS:
(A) LENGTH: 59 base pairs
(B) TYPE: nucleic acid ( C ) STRANDEDNESS: single
( D ) TOPOLOGY: linear ( x i ) SEQUENCE DESCRIPTION: SEQ ID NO:11:

GGCUUUUAGA AGUUAACCAG AGAAACACAC GGACUUCGUC CGUGGUAUAU UACCUGGUA    5 9

HUMAN PAPILLOMA VIRUS INHIBITION BY A HAIRPIN RIBOZYME

This is a continuation of application Ser. No. 08/242,665 filed on May 13, 1994 now abandoned.

TECHNICAL FIELD

The present invention relates to an RNA catalyst, i.e. ribozyme, which cleaves Human Papilloma virus into a fragment having a 5' hydroxyl and a fragment having a 2',3' cyclic phosphate. The products of the reaction described herein resemble those resulting from the natural hydrolysis of RNA.

BACKGROUND OF THE INVENTION

Pappillomaviruses are small DNA viruses that induce the hyperproliferation of epithelial cells. Approximately 70 different genotypes have been isolated from humans. Some types (1, 2, 4, and 7) are associated with benign squamous papillomas (warts; condylomas) in humans, while at least two types (16 and 18) have been associated with human neoplastic and preneoplastic lesions.[7]

In the United States, cervical cancer affects approximately 8.6 women per 100,000 each year. In woman, HPV-16 is frequently associated with latent infections, benign and premalignant cervical lesions (dysplasias/CIN) and half of invasive cervical carcinomas. In males, HPV-16 is associated with subclinical macular or clinical papular lesions. Bowenoid papulosis of the penis resembles carcinoma in situ. Cervical cancer, which kills at least 500,000 women worldwide each year, proceeds through progressive cellular changes from benign condylomata to high-grade dysplasias/CIN before developing into an invasive cancer. Over five billion health care dollars are spent in the United States each year on the detection and treatment of these lesions.

Epidemiology evidence indicates that up to 90% of all human and oral tumors harbor types of HPV that are able to immortalize primary human keratinocytes and transform rodent cells. The oncogene potential of HPV appears to be associated with products from two viral genes, E6 and E7. These products are required for the acquisition and maintenance of a transformed phenotype. The proteins encoded by these genes bind, with high affinity in neoplastic-associated types, to and neutralize the products of the Rb and p53 tumor suppressor cells.[15,20,21,22,23,24]

The current policy in genitourinary clinics is surgery for high-grade lesions due to the lack of superior alternatives. Cervical laser ablation therapy does not in the long term influence the natural history of cervical human papillomavirus-associated diseases in women. Interferons, per se, have been disappointing insofar as acute viral infection is concerned, usually because treatment cannot be started in time. Therefore, it has been assumed that any benefit with interferons is due to anti-proliferative effect and not due to antiviral.

Combination chemotherapy is also in use in cancer therapy, and cisplatin is one of the drugs of choice for cervical cancer, alone or in combination with other chemotherapy agents. However, the current success obtained with chemotherapy treatment is poor. The response rate for combination cisplatin and 5FU treatment in phase II studies in cervical cancer patients is only effective in 22% of the patients while the same combination produced an 88% response in squamous cell carcinoma of the head and neck.

The use of cytotoxic agents for cancer therapy has limitations because of toxic side effects and the development of multiple drug resistance. Therefore, there has been a consideration of a shift to therapy which does not involve direct toxic reaction, but which can modify the growth of tumor cells.

Current new therapeutic suggestions for treatment of HPV infections have centered on the use of antisense oligonucleotides to interrupt viral mRNA utilization.[7,23,24] However, antisense therapy is limited by stoichiometric considerations.[19]

Ribozymes are RNA molecules that possess RNA catalytic ability (see Cech et al., U.S. Pat. No. 4,987,071) that cleave a specific site in a target RNA. The number of RNA molecules that are cleaved by a ribozyme is greater than the number predicted by stochiochemistry.[11,26] This provides an advantage over the antisense technology.

Antisense therapy has two disadvantages when compared to ribozymes: (1) by its nature, the antisense molecule is not catalytic; and (2) antisense molecules are normally longer than the ribozyme target recognition sequence. This increases the likelihood of antisense molecules having a deleterious effect on similar mRNA sequences found in the same gene family.

Ribozymes have been designed on the "hammerhead" motif.[10] However, catalytic RNAs such as those that were designed based on the "hammerhead" model have several limitations which restrict their use in vitro and may forestall their use in vivo. For example, the temperature optimum for the reaction is 50°–55° C., which is well above physiological, and the kcat (turnover number) is only 0.5/min even at 55° C.[13,26] In addition, the Km is 0.6 µM,[26] meaning that the reaction requires high concentrations of substrate which makes it difficult, if not impossible, for the catalytic RNA to cleave low levels of target RNA substrate such as would be encountered in vivo.

A "hairpin" motif has been found to be more efficient than the "hammerhead" motif.[11,12] Further, hairpin ribozymes have been used to cleave targets on HIV.[16,28] However, ribozymes for one virus generally will not cleave other virus species. Not only do the ribozymes require specific target sequences for cleavage, they require modifications in the ribozyme structure itself to be able to efficiently cleave a specific target. Currently, there is no ribozyme that has been shown to cleave HPV RNA and no site has been identified in the HPV that is capable of cleavage by a ribozyme.

SUMMARY OF THE INVENTION AND ADVANTAGES

According to the present invention, synthetic catalytic RNAs, i.e. ribozymes, including a hairpin portion, a binding site for binding to a human papilloma virus either after viral base 434 or after base 419 and a cleavage site for cleaving the virus at the binding site have been constructed.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1:
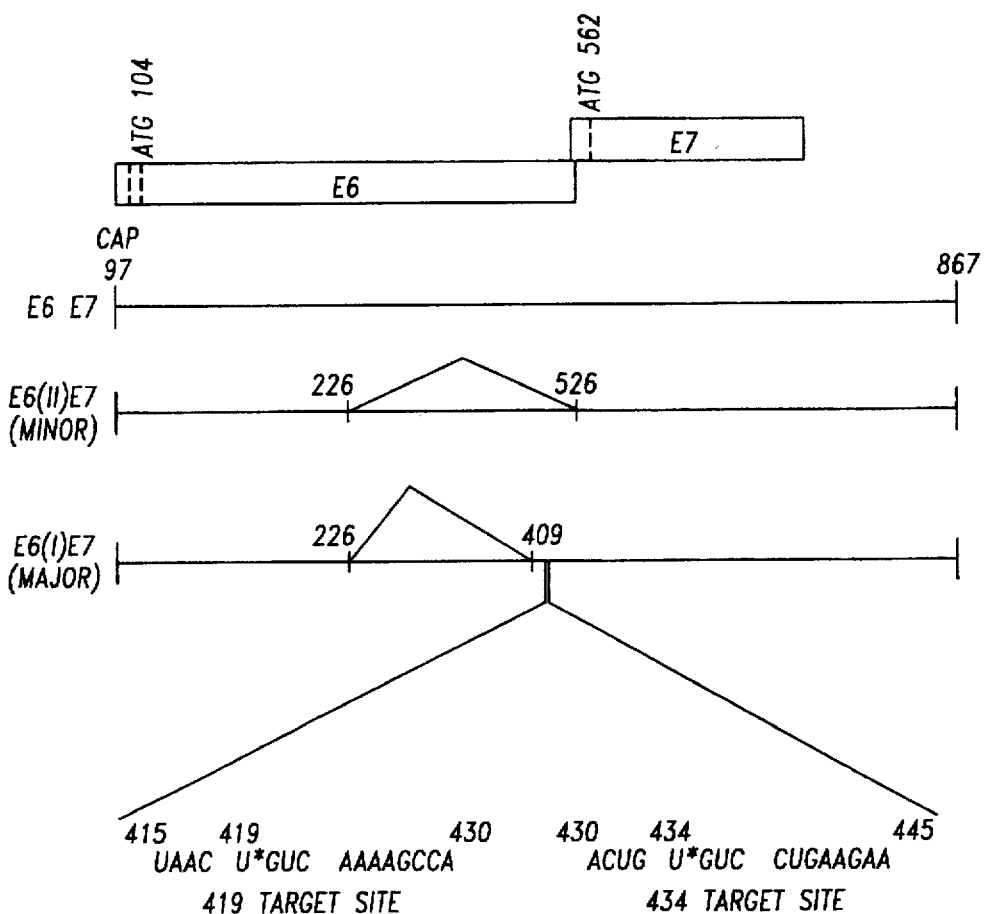
FIG. 1 is a diagram of the HPV target sites, shown are the location of the target sites selected for cleavage by the hairpin ribozyme, the target sites overlaps the mRNA for both the E6 and E7 region of HPV16, cleavage of this target site by the hairpin ribozyme occurs at the * after nucleotide 434 and nucleotide 419.

A hairpin ribozyme containing a tetraloop modification was designed, tested and shown to cleave a specific sequence in the primary transcript from human papilloma virus type 16. The cleavage sites immediately followed nucleotide 434 and 419, respectively, in the sequence of this virus. Optimization of the ribozyme was carried out showing that an 8 nt helix 1 was optimal for the 434 site and that a 7 nt helix i was optimal for the 419 site. The time course of the reaction showed nearly complete cleavage of the substrate.

Kinetic parameters for the 434 site were measured using standard Michaelis enzyme kinetic analysis. The Km for the reaction was 21 nM which shows very tight binding of the ribozyme and substrate. The kcat or turnover number was 0.083 min$^{-1}$ to give an overall catalytic efficiency (kcat/Km) of 4 $\mu M^{-1} min^{-1}$.

Kinetic parameters for the 419 site were also measured using standard Michaelis enzyme kinetic analysis. The Km for the reaction was 98 nM and the kcat or turnover number was 0.18 min$^{-1}$ to give an overall catalytic efficiency (kcat/Km) of 1.8 $\mu M^{-1} min^{-1}$.

The optimized target sites are shown in FIG. 1. Cleavage occurred after base 434 and after base 419, respectively, and before the GUC sequence shown as indicated in the diagram. This entire target sequence is part of the primary transcript (SEQ ID No:1) for the E6 and E7 regions of HPV16.[15,21] The cap for this mRNA is on nt 97. A splice donor exists at nt 226, and two splice acceptors exist at nt 409 and nt 526. As a result, three different E6-E7 mRNAs can be produced: E6E7, E6(I)E7, and E6(II)E7. E6E7 is the result of the full-length E6E7 transcript, in which the splice donor at nt 226 is not utilized. In E6E7, translation termination of E6 occurs at nt 557. E6(I)E7, the major transcript, is the result of utilization of the splice donor at nt 226 and the splice acceptor at nt 409, and its E6(I) translation termination signal is at nt 415. This gives a truncated E6 coding region and a full-length E7. E6(II)E7, the minor transcript, is the result of utilization of the splice donor at nt 226 and the splice acceptor at nt 526, and its E6(II) translation termination signal is at nt 541 to give a truncated E6 coding region and a full-length E7.[15]

An RNA catalyst (ribozyme) has been identified comprising an RNA sequence which can cleave, with great precision, HPV. The target sequences for cleavage by the ribozymes are present in the primary transcript E6E7, and E6(I)E7, the major transcript. Cleavage of these transcripts would have the effect of lowering the production of full-length E6 and E7 proteins, both of which appear to play a key role in keratinocyte transformation.[20]

Figure 2:
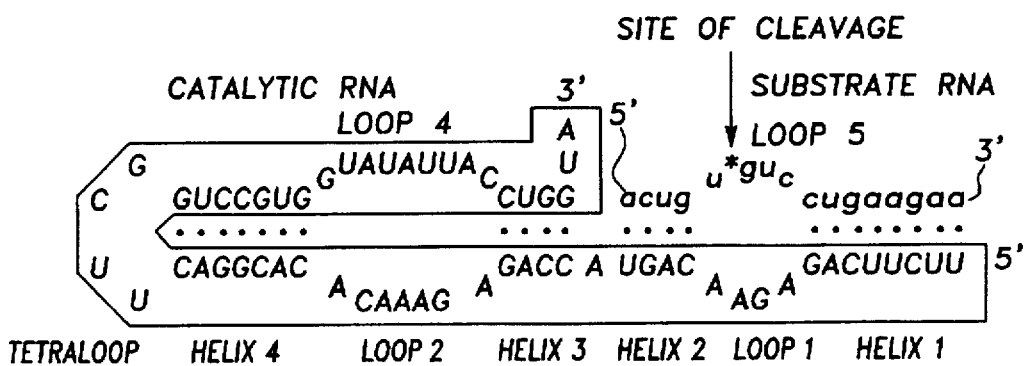
FIG. 2 is a diagram of the hairpin ribozyme with optimized helix 1 of 8 bp designed to cleave HPV-16 after position 434, shown are the sequences of the optimized ribozyme (RHPV) and substrate (SHPV), regions of base pairing between target substrate and ribozyme are labeled Helix 1 and Helix 2, regions of base pairing required in the "hairpin" portion of the catalyst are labeled Helices 3 and 4.

The hairpin ribozyme[12] designed to cleave after the 434 site in HPV is shown in FIG. 2 and is designated RHPV434. In the preferred embodiment, this hairpin ribozyme has the tetraloop modification as shown.[2] The GUU sequence of Loop 3 of the basic structure has been replaced by a tetraloop sequence GGAC (UUCG) GUCC which in the present invention has been shown to generate a very stable structure with high catalytic efficiency. In particular, the invention comprises certain synthetic RNA catalysts capable of cleaving an RNA substrate which contains the target sequences:

430-ACUG U*GUC CUGAAGA-444 (SEQ ID NO:2)
430-ACUG U*GUC CUGAAGAA-445 (SEQ ID NO:3)
430-ACUG U*GUC CUGAAGAAA-446 (SEQ ID NO:4)

Figure 6:
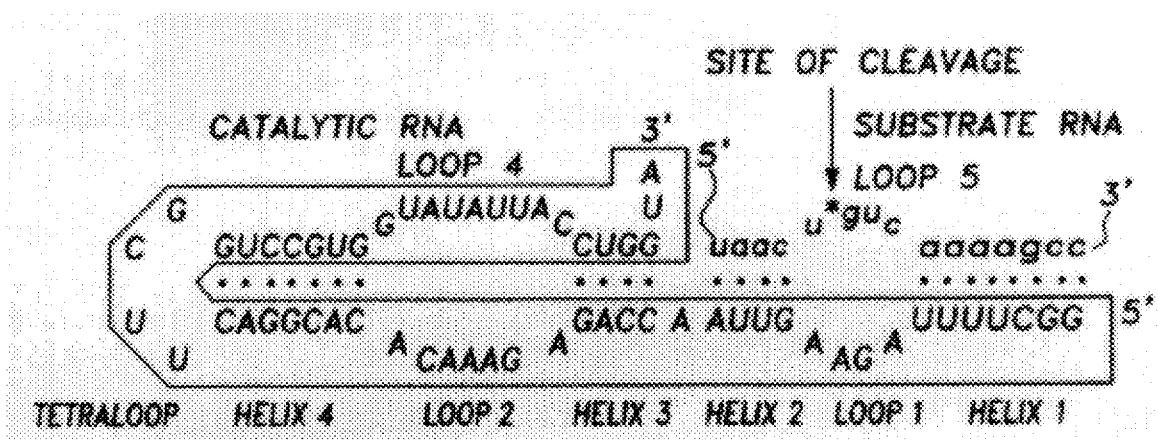
FIG. 6 is a diagram of the hairpin ribozyme with optimized helix 1 of 7 bp designed to cleave HPV-16 after position 419, shown are the sequences of the optimized ribozyme (RHPV) and substrate (SHPV), regions of base pairing between target substrate and ribozyme are labeled Helix 1 and Helix 2, regions of base pairing required in the "hairpin" portion of the catalyst are labeled Helices 3 and 4.

The hairpin ribozyme designed to cleave after the 419 site in HPV is shown in FIG. 6 and is designated RHPV419. In the preferred embodiment, this hairpin ribozyme also has the tetraloop modification as shown. The GUU sequence of Loop 3 of the basic structure has been replaced by a tetraloop sequence GGAC (UUCG) GUCC which in the present invention has been shown to generate a very stable structure with high catalytic efficiency. In particular, the invention comprises certain synthetic RNA catalysts capable of cleaving an RNA substrate which contains the target sequences:

415-UAAC U*GUC AAAAGC-428 (SEQ ID NO:7)
415-UAAC U*GUC AAAAGCC-429 (SEQ ID NO:8)
415-UAAC U*GUC AAAAGCCA-430 (SEQ ID NO:9)
415-UAAC U*GUC AAAAGCCAC-431 (SEQ ID NO:10)

"Synthetic RNA catalyst," as used herein, means a catalyst which is not a naturally-occurring RNA catalyst, although "synthetic catalysts" may be truncated or altered versions of naturally-occurring catalysts. "Synthetic catalyst" include catalysts synthesized in vitro and catalysts synthesized in vivo. In particular, "synthetic catalysts" can include catalysts produced by hosts transformed by a vector comprising a sequence coding for the catalyst.

RNA of any length and type may be used as the substrate as long as it contains the target sequence represented by the formula 5'-$F_1$-CS-$F_2$-3'. In this formula, CS is the cleavage sequence, i.e., a sequence of bases containing the site at which the catalyst cleaves the substrate. CS is a short sequence of bases which does not base pair with the ribozyme, and in the present invention CS preferably has the sequence 5'-NGUC-3', wherein N is any base, and the substrate is cleaved by the ribozyme between N and G to produce a fragment having an OH at the 5' end and a fragment having a 2',3' cyclic phosphate at the 3' end.

CS is flanked by two short base sequences $F_1$ and $F_2$ which do base pair with the RNA catalyst. $F_1$ is preferably at least 3 bases in length, most preferably 4 bases in length. $F_2$ is also preferably at least three bases in length, most preferably 6 to 12 bases in length.

Ribozymes, according to the present invention, also include a substrate binding portion and a "hairpin" portion. The substrate binding portion of the catalyst is represented by the following formula:

3'$F_4$-$L_1$-$F_3$-5' wherein, $F_3$ is a sequence of bases selected so that $F_3$ is substantially base paired with $F_2$ (Helix 1, FIGS. 2 and 6) when the catalyst is bound to the substrate;

$F_4$ is a sequence of bases selected so that $F_4$ is substantially base paired with $F_1$ when the catalyst is bound to the substrate (Helix 2, FIGS. 2 and 6);

The sequences of $F_3$ and $F_4$ are selected so that each contains an adequate number of bases to achieve sufficient binding of the RNA substrate to the RNA catalyst so that cleavage of the substrate can take place; and $L_1$ is a sequence of bases selected so that $L_1$ does not base pair with CS when the catalyst is bound to the substrate (Loop 1, FIGS. 2 and 6).

As used herein, "substantially base paired" means that greater than 65% of the bases of the two RNA sequences in questions are base paired, and preferably greater than 75% of the bases are base paired. "Substantially unpaired" means that greater than 65% of the bases of the two sequences in questions are not base paired, and preferably greater than 75% of the bases are not paired.

$F_3$ is preferably at least 3 bases in length, most preferably from 6 to 12 bases in length. $F_4$ is preferably from 3 to 5 bases in length, most preferably 4 bases in length.

$L_1$ is a short sequence of bases which preferably has the sequence 5'-AGAA-3' when CS has the sequence 5'-NGUC-3'. Further, when $L_1$ is 5'-AGAA-3' and CS is 5'-NGUC-3', then the first base pair between $F_1$ and $F_4$ adjacent to CS and $L_1$ is preferably G:C or C:G (FIGS. 2 and 6). Accordingly, in the present invention a preferred target sequence in a selected substrate contains the sequence 5'-BNGUC-3', wherein B is G, C, or U.[2]

The "hairpin" portion is a portion of the catalyst which folds into a hairpin-like configuration when the substrate-catalyst complex is modeled in two dimensions for minimum energy folding. This is shown in FIGS. 2 and 6. The "hairpin" portion is not an absolute hairpin in the sense that not all bases of the "hairpin" portion are base-paired. Indeed, it is necessary for the "hairpin" portion to have at least one substantially unpaired region so that the catalyst can assume a tertiary structure that allows for better, or optimal, catalytic activity.

The "hairpin" portion of the catalyst preferably has the sequence:

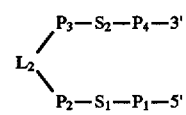

wherein, $P_1$ and $P_4$ are base sequences selected so that $P_1$ and $P_4$ are substantially base paired (Helix 3, FIGS. 2 and 6).

$P_1$ is covalently attached to $F_4$;

$S_1$ and $S_2$ are sequences selected so that $S_1$ (Loop 2) and $S_2$ (Loop 4) are substantially unpaired;

$P_2$ and $P_3$ are base sequences selected so that $P_2$ and $P_3$ are substantially base paired (Helix 4, FIGS. 2 and 6); and $L_2$ is a sequence of unpaired bases (Loop 3).

"Substantially base paired" and "substantially unpaired" have the same meanings as discussed above.

$P_1$ and $P_4$ are each preferably from 3 to 6 bases in length, and most preferably $P_1$ has the sequence 5'-ACCAG-3' and $P_4$ has the sequence 5'-CUGGUA-3'. It has been found that the A at the 5' end of 5'-ACCAG-3' (underlined) is not base paired to the U at the 3' end of 5'-CUGGMA-3' (underlined), and the unpaired A may act as a "hinge" (FIGS. 2 and 6).

$S_1$ and $S_2$ are each preferably from 4 to 9 bases in length, and most preferably $S_1$ has the sequence 5'-AGAAACA-3' and $S_2$ has the sequence 5'-GUAUAUUAC-3'.

Unexpectedly, it was found that the hairpin ribozyme as constructed for an HIV target sequence[16,28] was not as efficient as a hairpin ribozyme constructed with a "tetraloop" modification.

In the prior art the preferred sequence $P_2$ has the sequence 5'-CAC-3', $P_3$ has the sequence 5'-GUG-3' and $L_2$ has the sequence 5'-GUU-3'.[16]

In the preferred embodiment of the present invention, $L_2$, $P_2$, $P_3$ (FIGS. 2 and 6, Loop 3, Helix 4) are constructed to include the stable RNA hairpin sequence.

5'-GGAC UUCG GUCC -3' (SEQ ID No:5)

resulting in the "tetraloop" modification. As a result Helix 4 is extended by four base pairs over the prior art sequence listed hereinabove. Further, the GUU sequence of Loop 3 is replaced with the sequence UUCG. The resulting ribozyme is more active and more thermally stable than the non-modified ribozyme.

The structure of the present invention as shown in FIG. 2 for RHVP434 and described hereinabove can be diagrammatically represented by the formula:

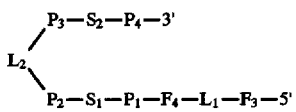

The complete sequence of the ribozyme of the preferred embodiment of the present invention is 5'-UUCUUCAGAGAACAGUACCAGAGAAACACA-
CGGACUUCG UCCGUGGUAUAUUACCUGGUA-
3' (SEQ ID No:6).

The structure of the present invention as shown in FIG. 6 for RHVP419 and described hereinabove can be diagrammatically represented by the formula:

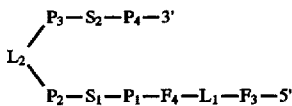

The complete sequence of the ribozyme of the preferred embodiment of the present invention is 5'-GGCUUUUAGAAGUUAACCAGAGAAACACAC-
GGACUUCG UCCGUGGUAUAUUACCUGGUA-3'
(SEQ ID No:11).

The ribozyme of the present invention which cleaves the RNA of HPV can be used as a therapeutic agent in the treatment of HPV infections which are associated with genital warts and genital neoplasms.

In the preferred embodiment, there are two methods for administering the therapeutic agent: gene therapy and a modification of antisense methodology. The therapeutic agent utilized in the present invention is administered in combination with other drugs or singly, consistent with good medical practice. The composition is administered and dosed in accordance with good medical practice taking into account the clinical condition of the individual patient, the site and method of administration, scheduling of administration, and other factors known to medical practitioners. The "effective amount" for purposes herein is thus determined by such considerations as are known in the art.

(1) Human gene therapy.[14] The coding sequence for the HPV16 specific ribozyme is cloned into a vector as described herein. A U6 promoter has been cloned into the vector and is positioned immediately before the ribozyme coding region. The U6 promoter is a eukaryotic pol III promoter capable of driving transcription of the ribozyme using the host cell's RNA polymerase III.[6] The use of a retroviral vector for carrying the encoded ribozyme will aid in the integration of the ribozyme coding sequence within the cell's genomic DNA, thus providing long-term production of the anti-HPV16 ribozyme within the cell.[4]

To deliver the ribozyme-encoding vector to the target cells, a Lipofectin-based liposomal delivery system will be used. The use of liposomes will aid in getting the vector-ribozyme DNA to the cell without being degraded since the liposome acts as a protective barrier from nucleases.[25] The cells will take in the vector-containing liposomes via the naturally occurring process of endocytosis. The advantage of using the Lipofectin reagent is that it allows the liposome, once taken into the cell, to bypass degradation by lysosomal enzymes which is the usual fate of endocytic material.[9] In a preferred embodiment, ribozymes directed against either or both of E6 and E7 would be administered in combination with immunological agents such as LAK cells or chemotherapeutic agents such as cisplatin, which now has limited use in cervical cancer. Delivery of a ribozyme to the cervical area would be by either painting or injection.

The above discussion provides a factual basis for the use of ribozymes as a therapy for HPV infections. The methods used with and the utility of the present invention can be shown by the following examples.

EXAMPLES

Materials and Methods:

Enzymes and Chemicals. All restriction enzymes used were from either Bethesda Research Laboratories (BRL) or Boehringer Mannheim Biochemicals. The buffers for restriction enzymes were supplied by the manufacturer. T4DNA ligase and the sequencing kit were obtained from Pharmacia. The in vitro transcription kit and relevant enzymes were obtained from Promega. Bovine calf serum, antibiotics (penicillin and streptomycin), L-glutamine, sodium pyruvate, phosphate-buffered saline (PBS) and Dulbecco modified Eagle medium (DMEM) were purchased from GIBCO.

Recombinant DNA techniques unless stated otherwise were performed as described in Sambrook et al.[18] incorporated herein by reference.

Enzymes and Chemicals: T4 DNA Ligase and all restriction enzymes used were from Bethesda Research Laboratories (BRL). T7 RNA Polymerase used was manufactured by US Biochemicals (USB). With the exception of T7 RNA Polymerase, the buffers for enzymes used were supplied by the manufacturer. The T7 RNA Polymerase transcription buffer consisted of the following: 40 mM Tris pH 8.0, 6 mM $MgCl_2$, 5 mM DTT, 1 mM Spermidine, 1% Triton-X 100. Synthetic DNA templates used for in vitro transcriptions and cloning were produced using an Applied Biosystems 392 DNA synthesizer.

Cleavage of HPV substrates was carried out in 12 mM $MgCl_2$, 2 mM spermidine and 40 mM Tris pH7.5 using methods previously published.[11] All reactions were carried out at 37° C., with 25 nM ribozyme and 50 nM substrate for 60 minutes unless otherwise indicated. The reference reaction was native (−)sTRSV sequence S17/R53 at 10 nM and 100 nM for the times shown.[11]

$P^{32}$ labelling: Substrate and ribozymes were labelled with a $P^{32}$-CTP by transcription from synthetic DNA templates using T7 RNA polymerase as previously described[11] and reaction products separated on 15–18% polyacrylamide gels in 7M urea.

Construction of the ribozyme: The ribozyme was constructed by T7 transcription from complementary synthetic DNA templates. This was carried out as previously described.[11]

Construction of plasmids and Vectors containing RHPV: Coding and non-coding strands for RHPV were synthesized and HPLC purified. The strands included an Eco RI site, the ribozyme coding region, a poly-T termination signal for RNA Polymerase III, and a Bam HI site. The two strands were then annealed by adding an equimolar amount of each and incubating in $H_2O$ at 90° C. for 5 minutes, then allowed to slowly cool down to room temperature over a 30-minute period. The resulting double-stranded fragment was digested with Eco RI and Bam HI. The digestion products were run on an agarose gel, and the ribozyme coding fragment was isolated and purified.

The plasmid $PHC^1$ was digested with Eco RI and Bam HI, and the fragment was isolated and purified as above. The RHPV434 or RHVP419 fragment was then ligated into pHC, and the ligation mixture was used to transform competent DH5α bacterial cells. Single colonies were selected and grown in CircleGrow bacterial media, and plasmids extracted and purified by Sambrook's miniprep protocol.[18] The plasmids were screened for incorporation of the RHPV434 or RHVP419 insert. A colony that incorporated the insert was then sequenced using the Sequenase Version 2.0 enzymes and protocol to verify proper DNA sequence. The resulting plasmid was termed pHC-434 or pHC-419 respectively The ribozymes are cloned into a Moloney based retroviral expression vector for in vivo testing in human cells transformed with HVP-16. The cloning scheme is as follows. The ribozyme oligos are synthesized with a Pol III termination signal and EcoR1/BamH1 termini. These are then cloned into pHC,[1] the standard bacterial expression vector used in a preferred embodiment. The ribozyme is cut out with EcoR1 HindIII and cloned into pU6 which is a Bluescript vector containing a mouse U6 promotor.[6] The insert containing the U6 promoter is then cloned into the BamH1 site of pZIP-NeoSV(X).[3]

pHC-434 and pMU6, a plasmid which contains an RNA polymerase III promoter region[6] were digested with Eco RI and Hind III. The RHPV434 fragment, which retained the hairpin cassette region, and the pMU6 fragment were isolated and purified as described above. Ligation and bacterial transformation of the two fragments was carried out as described above. Colonies were screened and sequenced as described above. The resulting plasmid was termed pMU6-434.

Screening of HPV Sequence (SEQ ID No:1) for cleavage site: HPV16 sequence data was obtained through Gen Bank. HPV16 E6 and E7 regions were inspected for potential target sequences as described above. All potential sites containing potential target sequences were tested, and ribozymes that showed significant catalytic activity were further developed. RHPV434 and RHVP419 are examples of ribozymes that showed significant catalytic activity.

Example 1

In the preferred embodiment of the present invention as shown in FIG. 2, Loop 3 and Helix 4 are constructed to include the stable RNA hairpin sequence 5'- GGAC UUCG GUCC -3' (SEQ ID No:5)

resulting in the "tetraloop" modification-[5,27] As a result Helix 4 is extended by four base pairs over the non-modified sequence. Further, the GUU sequence of Loop 3 is replaced with the sequence UUCG.

To determine the activity of the ribozyme, it is added to a substrate RNA at a ratio of 1:30 and the time course of cleavage studied as parameters are varied. The reaction is carried out in 12 mM $MgCl_2$, 40 mM Tris pH7.5 and 2 mM spermidine over 150 minutes. For temperature dependence, the rate of cleavage of a ribozyme containing the tetraloop modification is tested over a temperature range and compared to the control reaction at 37° C. The reaction products are analyzed on polyacrylamide/urea gels. The bands are cut out and counted in a liquid scintillation counter. In the control reaction only 2% of the substrate remains after 150 min. indicating that the ribozyme must interact with multiple substrates during the course of the reaction since there were 30 times as much substrate as ribozyme. Further, the amount of the ribozyme remains the same and unaltered as expected of a catalyst.

In the temperature dependent study of the tetraloop modification compared to the prior art the activity of the ribozyme was measured at 20° C., 27° C., 33° C., 37° C., 41° C. and 45° C.

The reaction showed a temperature dependence similar to that which would be expected of a reaction involving base paired RNA molecules. The Arrhenius plot of the data gives a temperature optimum of 37° C. for the reaction. Higher temperatures reduce the reaction rate with a very rapid rate reduction about 41° C. consistent with a melting out of the catalytic RNA structure. At 50° C., no reaction was detectable. The reaction rate at temperatures below 37° C. showed a linear reciprocal temperature dependence consistent with a classical lowering of the energy of activation for the reaction. The slope of the line in the Arrhenius plot gave an energy of activation of 19 Kcal/mole which is close to that found for catalysts fitting the "hammerhead" cleavage mechanism (13.1 Kcal/mole).[26]

The example shows that a ribozyme with the tetraloop modification is more active and more thermally stable than the prior art. This form of the ribozyme remains active at 45° C. while the nonmodified ribozyme lost most of its activity at this temperature.

It was concluded from this experiment that Loop 3 does not have a conserved or invariant base sequence and that Helix 4 can be extended into Loop ° 3 by at least four base pairs with no loss of activity. The four additional base pairs in Helix 4 provide helix stabilization of this region. The secondary folding energy of Helix 4 and Loop 3 in the prior art structure is +0.6 Kcal/mole, while that of the ribozyme having the extended Helix 4 and Loop 3 of sequence UUCG (tetraloop) of the present invention was determined to be −11.1 Kcal/mole. Thus the presence of the tetraloop sequence increases the folding energy by 11.7 Kcal/mole.

Example 2

Figure 3:
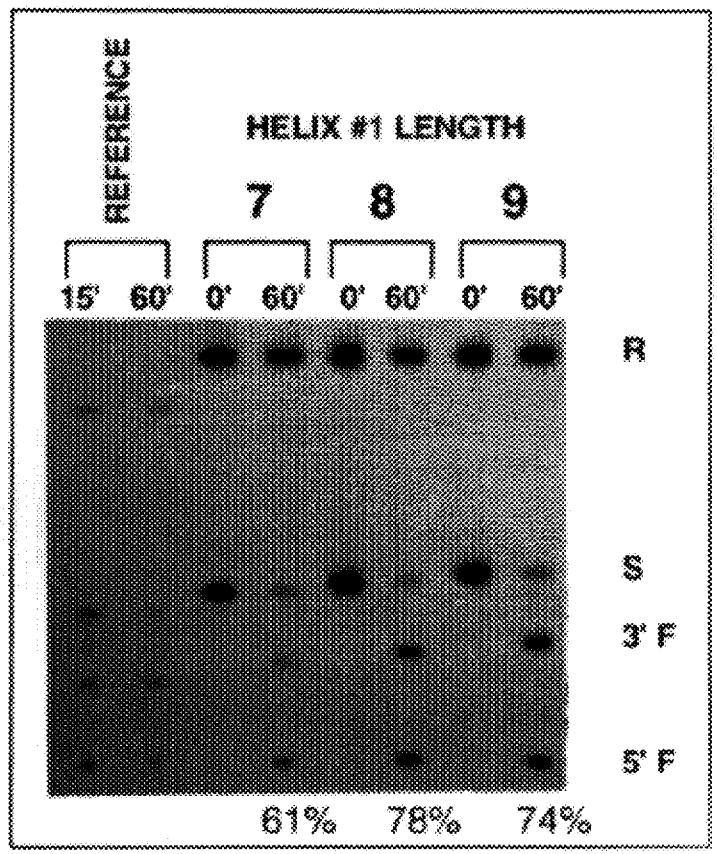
FIG. 3 is an autoradiograph of the results of cleavage of HPV substrates after the 434 site by the present invention with helix 1 lengths of 7 bp, 8 bp, and 9 bp as shown, reference controls were ribozyme R53 and substrate S17 (lanes 1 and 2), the reaction was at 37° C. with 25 nM ribozyme and 50 nM substrate for 60 minutes, reference reaction was native (−)sTRSV sequence S17/R53 at 10 nM and 100 nM for the times shown;[11]

The Cleavage Reaction and optimization of helix 1 length for RHVP434. A cleavage study was undertaken to optimize the length of Helix 1. FIG. 3 shows bands on a denaturing polyacrylamide gel identifying the ribozyme, substrate and cleavage products. Three substrates were cleaved by the ribozyme, each with a different length helix 1. The substrates were as follows:

| Substrate | Helix 1 Length | % Cleaved |
|---|---|---|
| 430-ACUG U•GUC CUGAAGA-444 (SEQ ID No:2) | 7 | 5.4 |
| 430-ACUG U•GUC CUGAAGAA-445 (SEQ ID No:3) | 8 | 6.7 |
| 430-ACUG U•GUC CUGAAGAAA-446 (SEQ ID No:4) | 9 | 6.5 |

The most efficiently cleaved substrate was that which had an 8 bp helix 1 (SEQ ID No:3) and was used for all further studies. It is referred to as SHPV and the corresponding ribozyme is referred to as RHPV-434 (FIG. 2).

Figure 4A:
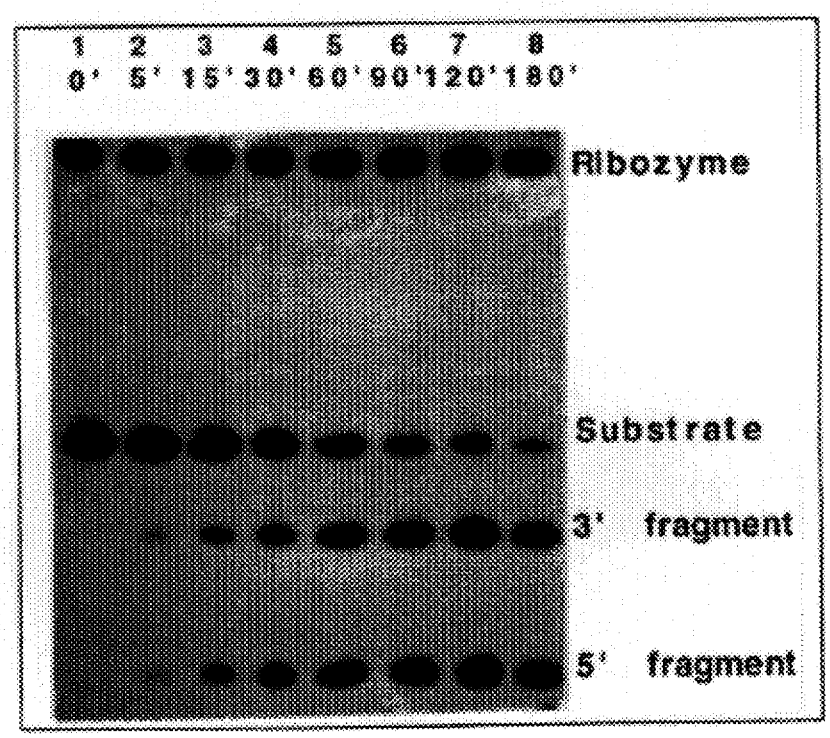
FIGS. 4(A) and 4(B) present the results of a time course of the cleavage by RHPV434, (A) is an autoradiograph of the cleavage results at each time point and (B) is a graph of the results from 4A, cleavage conditions were that same as in FIG. 3 using [R]=25 nM and [S]=100 nM for the times shown.
Figure 4B:
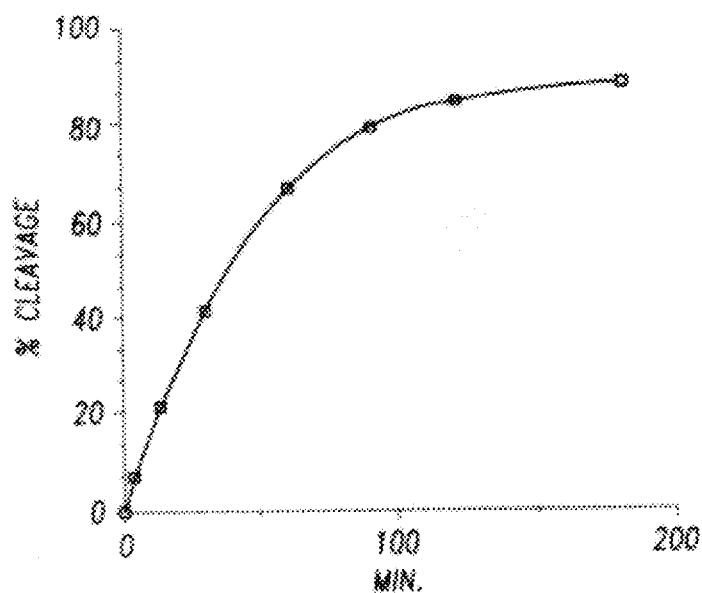

Time course of cleavage. The time course for cleavage of SHPV by RHPV-434 was done over a 180 min period (FIG. 4). The ribozyme efficiently cleaved the substrate to 88% completion.

Figure 5A:
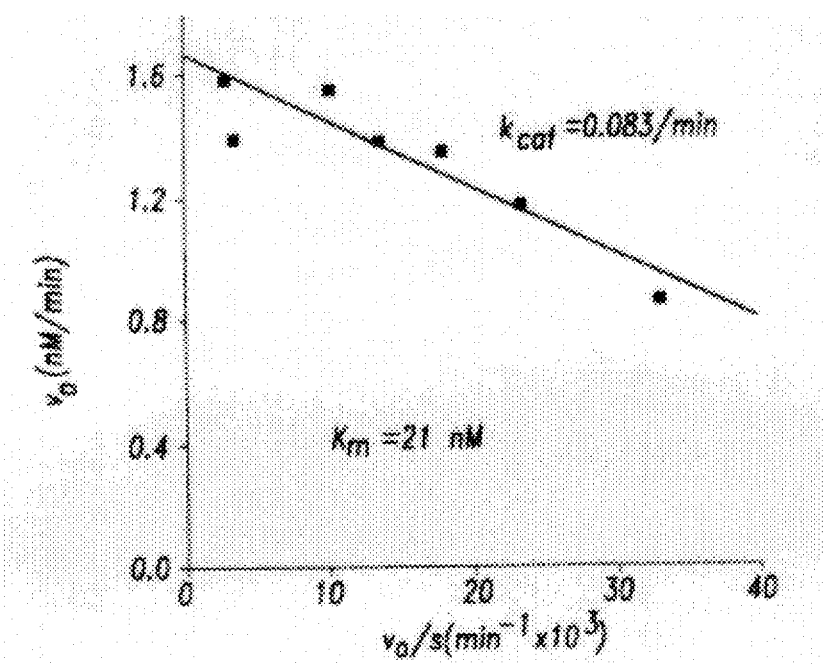
FIGS. 5(A) and 5(B) present the results of a kinetic analysis of cleavage by RHPV434, (A) is a graph of the results from 4B and (B) is an autoradiograph of the cleavage results after 10 minutes at each concentration of [S], with cleavage conditions as in FIG. 3 using [R]=20 nM and [S] of 400 nM (lane 1), 200 nM (lane 2), 150 nM (lane 3), 100 nM (Lane 4), 75 nM (lane 5), 50 nM (lane 6), and 25 nM (lane 7)
Figure 5B:
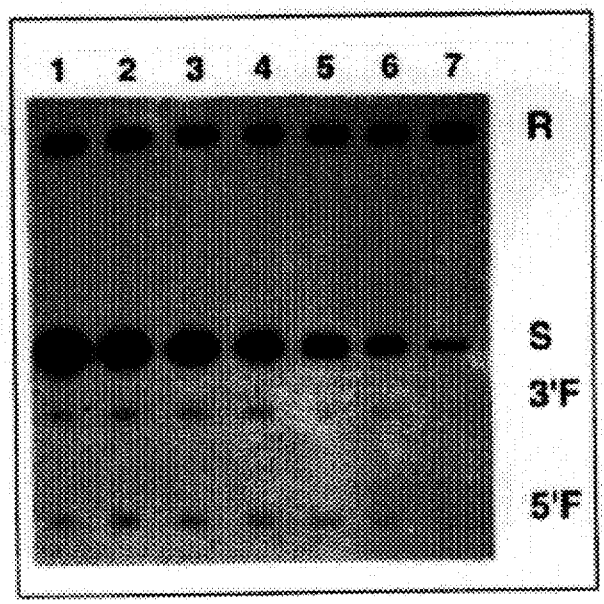

Kinetic Parameters of Cleavage. A Michaelis kinetic analysis of the reaction was carried out using limiting ribozyme and excess substrate for constant ribozyme concentration and varying substrate concentrations to measure initial velocities (FIG. 5). The $K_m$ for the reaction was 21 nM and $k_{cat}$ or turnover number was 0.083 $min^{-1}$. This gives an overall catalytic efficiency (kcat/Km) of 4 $\mu M^{-1} min^{-1}$ which is about 7% that of the original native hairpin sequence.[11]

Example 3

Figure 7:
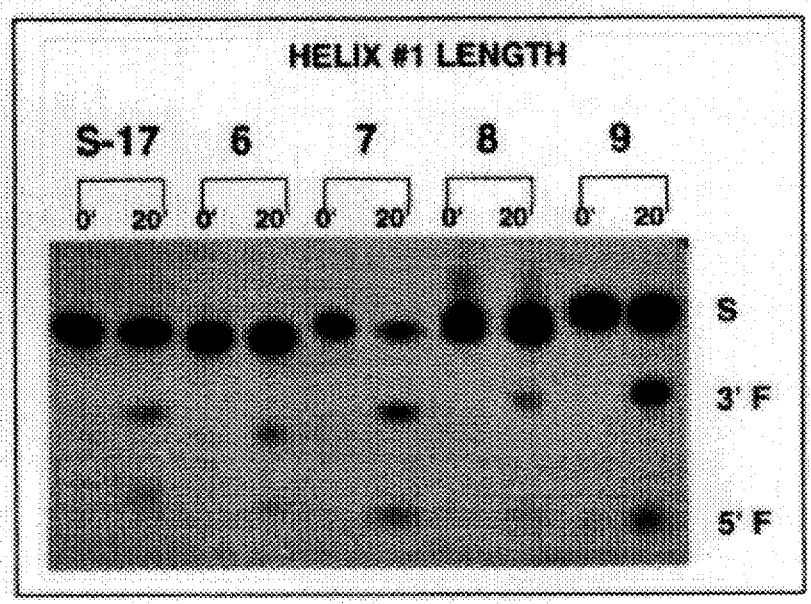
FIG. 7 is an autoradiograph of the results of cleavage of HPV substrates after the 419 site by the present invention with helix 1 lengths of 6 bp, 7 bp, 8 bp, and 9 bp as shown, reference controls were ribozyme R53 and substrate S17 (lanes 1 and 2), the reaction was at 37° C. with 25 nM ribozyme and 50 nM substrate for 60 minutes, reference reaction was native (−)sTRSV sequence S17/R53 at 10 nM and 100 nM for the times shown;[11]

The Cleavage Reaction and optimization of helix 1 length for RHVP419. A cleavage study was undertaken to optimize the length of Helix 1. FIG. 7 shows bands on a denaturing polyacrylamide gel identifying the ribozyme, substrate and cleavage products. Four substrates were cleaved by the ribozyme, each with a different length helix 1. The substrates were as follows:

| Substrate | Helix 1 Length | % Cleaved |
|---|---|---|
| 415-UAAC U*GUC AAAACC-428 (SEQ ID NO:7) | 6 | 7.5 |
| 415-UAAC U*GUC AAAAGCC-429 (SEQ ID No:8) | 7 | 62.8 |
| 415-UAAC U*GUC AAAAGCCA-430 (SEQ ID No:9) | 8 | 12.1 |
| 415-UAAC U*GUC AAAAGCCAC-431 (SEQ ID No:10) | 9 | 28.9 |

The most efficiently cleaved substrate was that which had a 7 bp helix 1 (SEQ ID No:8) and was used for all further studies. It is referred to as SHPV and, the corresponding ribozyme is referred to as RHPV-419 (FIG. 6).

Figure 8A:
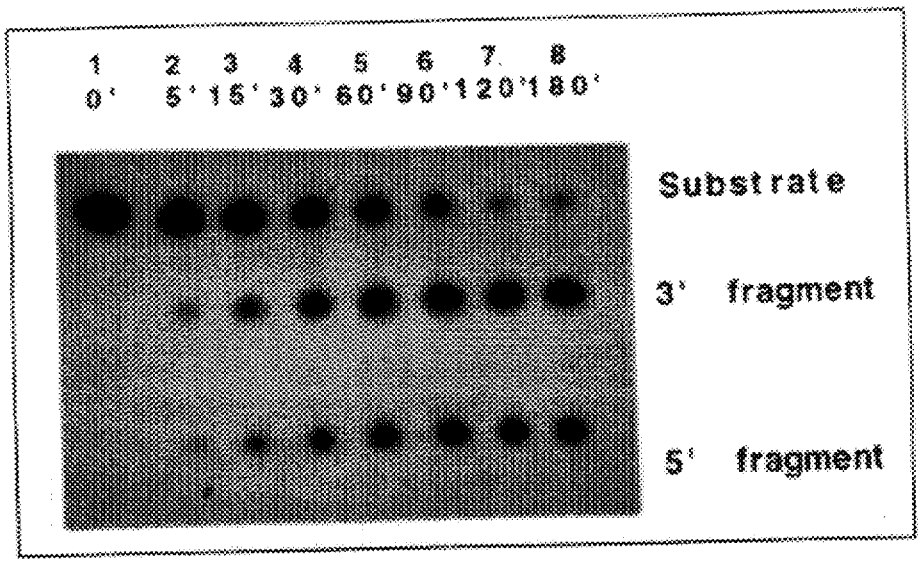
FIGS. 8(A) and 8(B) present the results of a time course of the cleavage by RHPV419, (A) is an autoradiograph of the cleavage results at each time point and (B) is a graph of the results from 8A, cleavage conditions were that same as in FIG. 3 using [R]=25 nM and [S]=100 nM for the times shown.
Figure 8B:
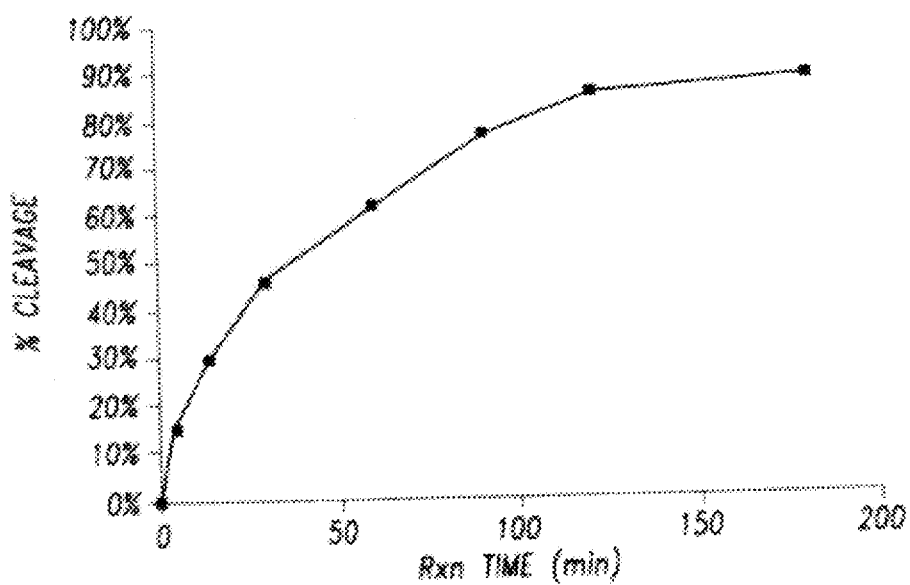

Time course of cleavage. The time course for cleavage of SHPV by RHPV-419 was done over a 180 min period (FIG. 8). The ribozyme efficiently cleaved the substrate to 88% completion.

Figure 9A:
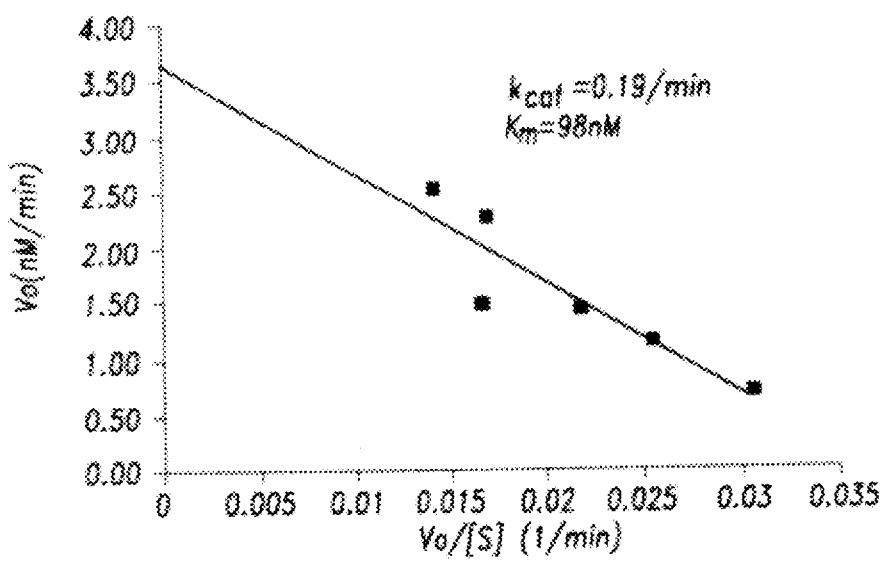
FIGS. 9(A) and 9(B) present the results of a kinetic analysis of cleavage by PaPV419, (A) is a graph of the results from 9B and (B) is an autoradiograph of the cleavage results after 10 minutes at each concentration of [S], with cleavage conditions as in FIG. 3 using [R]=20 nM and [S] of 200 nM (lane 1), 150 nM (lane 2), 100 nM (Lane 3), 75 nM (lane 4), 50 nM (lane 5), and 25 nM (lane 6), Lanes 7 and 8 were controls for reaction completion and were zero minute and one hour respectively for [S] of 20 nM.
Figure 9B:
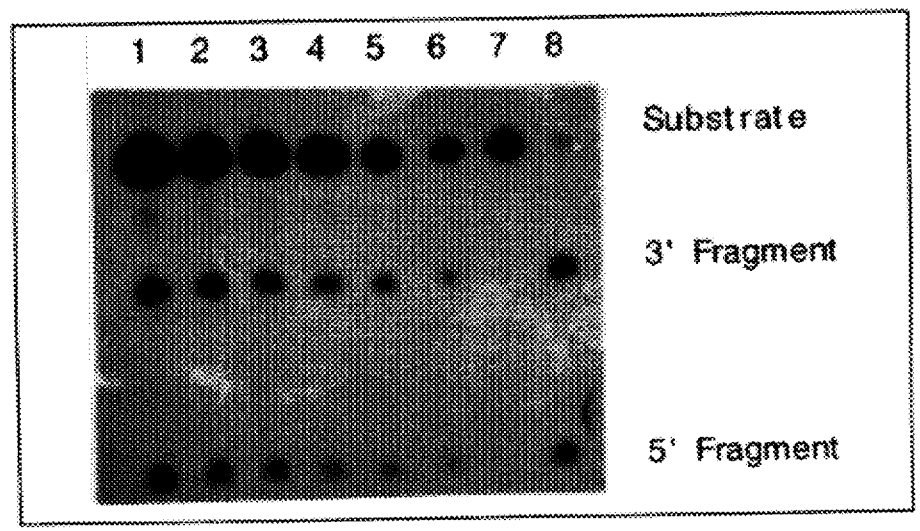

Kinetic Parameters of Cleavage. A Michaelis-Menton kinetic analysis of the reaction was carried out using limiting ribozyme and excess substrate for constant ribozyme concentration and varying substrate concentrations to measure initial velocities (FIG. 9). The $K_m$ for the reaction was 98 nm and $k_{cat}$ or turnover number was 0.18 $min^{-1}$. This gives an overall catalytic efficiency (kcat/Km) of 1.8 $\mu M^{-1} min^{-1}$ which is about 3% that of the original native hairpin sequence.[11]

Throughout this application various publications are referenced by citation or number. Citations for the publications referenced by number are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

1. Altschuler, 1992, Gene, 122:85–90
2. Anderson et al., 1994, Nuc. Acids Res. (in press)
3. Cepko et al., 1984, Cell 37:1053–1062
4. Chatterjee and Wong, 1993, Methods: Companion to Methods in Enzymology 5(1):51–59
5. Cheong et al., 1990, Nature, 346:680–82
6. Das, 1988, EMBO J. 7(2):503–512
7. Dipaolo et al., 1993, Critical Reviews in Oncogenesis (in press)
8. Doeberitz et al.
9. Felgner et al., 1993, Methods: Companion to Methods in Enzymology 5(1):67–75
10. Forster and Symons, 1987, Cell 49:211–220
11. Hampel and Tritz, 1989, Biochem. 28:4929–4933
12. Hampel et al., 1990, Nucleic Acids Research 18:299–304
13. Haseloff and Gerlach, 1988, Nature 334:585
14. Mulligan, 1993, Science 260:926–932
15. Nasseri, 1991, Virol., 184:136
16. Ojwang et al.
17. Rossi, 1993, Methods: companion to Methods in Enzymology 5:1–5
18. Sambrook, 1989, Molecular Cloning: A Laboratory Manual, Cold Spring Harbor, Sections 1.25–1.28, 1.60–1.61, 1.68–1.69, 1.82–1.84, 6.9–6.13, 6.46–6.48
19. Sarver et al., 1990, Gene Regulation and Aids, pp. 305–325
20. Sedanan et al., 1991, J. Virololgy65:4860–4866
21. Smotkin and Wettstein, 1989, J. Virology 63:1441–1447
22. Smotkin and Wettstein, 1986, J. Virology 63:1441–1447
23. Steele et al.
24. Storey et al.
25. Sullivan, 1993, Methods: Companion to Methods in Enzymology, 5(1):61–66
26. Uhlenbeck, 1987, Nature 328:596–600
27. Varani et al. Biochem., 30:3280–89 (1991)
28. Yu et al

What is claimed is:

1. A synthetic hairpin ribozyme which binds to and cleaves a target site in a human papilloma virus transcript, said target site selected from the group consisting of target sites represented by: SEQ ID NO: 2, SEQ ID NO: 3, SEQ ID NO: 4, SEQ ID NO: 7, SEQ ID NO: 8, SEQ ID NO: 9, and SEQ ID NO: 10.

2. A synthetic hairpin ribozyme as in claim 1 which includes a tetraloop consisting of SEQ ID NO: 5.

3. A synthetic ribozyme as in claim 1 consisting of the complete sequence as set forth in SEQ ID No:6.

4. A synthetic ribozyme as in claim 1 consisting of the complete sequence as set forth in SEQ ID No:11.

5. A method of constructing a ribozyme to cleave a human papilloma virus transcript comprising the step of constructing a hairpin ribozyme wherein a binding site on the ribozyme includes a sequence noncomplementary to the cleavage site on a human papilloma virus and a binding region complementary to the sequences on either side of the cleavage site where the binding regions are complementary to sequences selected from the group consisting of: SEQ ID NO: 2, SEQ ID NO: 3, SEQ ID NO: 4, SEQ ID NO: 7, SEQ ID NO: 8, SEQ ID NO: 9, and SEQ ID NO: 10.

6. A method of constructing a ribozyme to cleave a human papilloma virus transcript according to claim 5 wherein the step of constructing said hairpin ribozyme includes incorporating a tetraloop having the sequence set forth in SEQ ID NO: 5.

7. A vector comprising a DNA sequence coding for said ribozyme according to claim 1, the DNA being operatively linked to expression control sequences.

8. A host cell transformed with a vector according to claim 7 and which is capable of expressing said ribozyme encoded by said vector.

* * * * *